United States Patent
Park et al.

(10) Patent No.: US 12,156,727 B2
(45) Date of Patent: Dec. 3, 2024

(54) DEEP LEARNING-BASED COUGH RECOGNITION METHOD AND DEVICE

(71) Applicants: Korea Advanced Institute of Science and Technology, Daejeon (KR); SM Instruments Co., Ltd., Daejeon (KR)

(72) Inventors: Yong Hwa Park, Daejeon (KR); Gyeong Tae Lee, Daejeon (KR); Hyeonuk Nam, Daejeon (KR); Seonghu Kim, Daejeon (KR); Young Key Kim, Daejeon (KR); In Kwon Kim, Daejeon (KR); Kwang Hyun Lee, Daejeon (KR); Jae Sun Lee, Daejeon (KR); Sung Hyo Park, Daejeon (KR)

(73) Assignees: KOREA ADVANCED INSTITUTE OF SCIENCE AND TECHNOLOGY, Daejeon (KR); SM INSTRUMENTS CO., LTD., Daejeon (KR)

( * ) Notice: Subject to any disclaimer, the term of this patent is extended or adjusted under 35 U.S.C. 154(b) by 212 days.

(21) Appl. No.: 18/051,137

(22) Filed: Oct. 31, 2022

(65) Prior Publication Data
US 2023/0078404 A1   Mar. 16, 2023

Related U.S. Application Data

(63) Continuation of application No. PCT/KR2021/008592, filed on Jul. 6, 2021.

(30) Foreign Application Priority Data

Jul. 9, 2020 (KR) .......... 10-2020-0084770
Nov. 27, 2020 (KR) .......... 10-2020-0163070

(51) Int. Cl.
*A61B 5/08* (2006.01)
*A61B 5/00* (2006.01)
*A61B 5/11* (2006.01)

(52) U.S. Cl.
CPC .......... *A61B 5/0823* (2013.01); *A61B 5/1128* (2013.01); *A61B 5/6889* (2013.01); *A61B 2562/0204* (2013.01)

(58) Field of Classification Search
None
See application file for complete search history.

(56) References Cited

U.S. PATENT DOCUMENTS

| | | | |
|---|---|---|---|
| 7,727,161 B2 | 6/2010 | Coyle et al. | |
| 10,042,038 B1 | 8/2018 | Lord | |
| 2007/0276278 A1 | 11/2007 | Coyle et al. | |
| 2020/0015709 A1 | 1/2020 | Peltonen et al. | |
| 2020/0411036 A1* | 12/2020 | Daimo | G06V 40/20 |

FOREIGN PATENT DOCUMENTS

| | | |
|---|---|---|
| CN | 101894551 | 5/2012 |
| KR | 10-2019-0084460 | 7/2019 |
| KR | 10-2019-0113390 | 10/2019 |
| KR | 10-2043341 | 11/2019 |
| KR | 10-2020-0017940 | 2/2020 |

* cited by examiner

*Primary Examiner* — Mark Fischer
(74) *Attorney, Agent, or Firm* — NIXON PEABODY LLP

(57) ABSTRACT

Provided is a cough recognition method and device, which can detect cough sounds from an audio signal, and not only can detect coughs but also can track the location at which the cough sounds are generated by calculating the location of a sound source.

6 Claims, 13 Drawing Sheets

Constant-Q Transform (CQT)

Mel-frequency cepstral coefficients (MFCC)

DEEP LEARNING-BASED COUGH RECOGNITION METHOD AND DEVICE

CROSS-REFERENCES TO RELATED APPLICATION(S)

This U.S. non-provisional application is a continuation application of PCT International Application PCT/KR2021/008592, which has an International filing date of Jul. 6, 2021, and claims priorities under 35 U.S.C. 119 to Korean Patent Application No. 10-2020-0084770, filed on Jul. 9, 2020, and Korean Patent Application No. 10-2020-0163070, filed on Nov. 27, 2020, in the Korean intellectual property office, the disclosures of which are herein incorporated by reference in its entirety.

BACKGROUND

Due to the Corona Virus Disease (COVID)-19 situations, the demand for technology for detecting infectious diseases in a contactless manner is increasing. The main symptoms of COVID-19 include fever and cough. Currently, equipment, such as a thermal imaging camera, is widely used to detect fever but there is no widely used equipment to detect cough.

Also, in the related art for detecting cough, it is difficult to classify cough sound and other sound in an environment in which background noise is present. Also, although the cough sound is recognized, it is not possible to track and observe a location at which the cough sound occurs, a person who coughs, and a cough count.

SUMMARY

Example embodiments of the following description relate to a deep learning-based cough recognition method for recognizing cough and more particularly, to a method and device for tracking cough sound in real tame using an artificial intelligence (AI)-based cough recognition model.

Example embodiments provide a cough recognition method and device that may detect cough sound and also track a location at which the cough sound occurs by detecting the cough sound from audio signals and by calculating a location of a sound source.

According to at least one example embodiment, there is provided a cough recognition device including a plurality of microphone arrays each configured to receive audio signals; a camera module configured to generate a camera image; and at least one processor. The at least one processor is configured to collect the audio signals through the plurality of microphone arrays and display a location of a sound source on the camera image, to determine whether the audio signals include cough sound using a deep learning model, and to when the audio signals include the cough sound, further display a cough indication in association with the location of the sound source displayed on the camera image.

According to an aspect, to display the location of the sound source, the at least one processor may be configured to collect the audio signals input through the plurality of microphone arrays through data acquisition (DAQ), and to display the location of the sound source recognized through a beamforming process for the collected audio signals on the camera image in a form of a contour line.

According to another aspect, the deep learning model may include a binary classification model configured to receive and learn learning data including data augmented cough sound with background noise and to output whether the input audio signals include the cough sound.

According to still another aspect, to determine whether the audio signals include the cough sound using the deep learning model, the at least one processor may be configured to store the collected audio signals in a data stack to be accumulated in a preset time section, to extract acoustic features from the audio signals accumulated in the preset time section, and to input the extracted acoustic features to the deep learning model and determine whether the audio signals include the cough sound based on an output value of the deep learning model.

According to at least one example embodiment, there is provided a cough recognition method including generating a camera image through a camera module; collecting audio signals through a plurality of microphone arrays and displaying a location of a sound source on the camera image; determining whether the audio signals include cough sound using a deep learning model; and when the audio signals are determined to include the cough sound, further displaying a cough indication in association with the location of the sound source displayed on the camera image.

According to an aspect, the displaying of the location of the sound source may include collecting the audio signals input through the plurality of microphone arrays through DAQ, and displaying the location of the sound source recognized through a beamforming process for the collected audio signals on the camera image in a form of a contour line.

According to another aspect, the deep learning model may include a binary classification model configured to receive and learn learning data including data augmented cough sound with background noise and to output whether the input audio signals include the cough sound.

According to still another aspect, the determining whether the audio signals include the cough sound using the deep learning model may include storing the collected audio signals in a data stack to be accumulated in a preset time section; extracting acoustic features from the audio signals accumulated in the preset time section; and inputting the extracted acoustic features to the deep learning model and determining whether the audio signals include the cough sound based on an output value of the deep learning model.

According to at least one example embodiment, there is provided a computer-readable record medium in which a computer program to execute the method in a computer device is recorded.

According to example embodiments, it is possible to detect cough sound from audio signals and also to track a location at which the cough sound occurs by calculating a location of a sound source.

DETAILED DESCRIPTION

Figure 1:
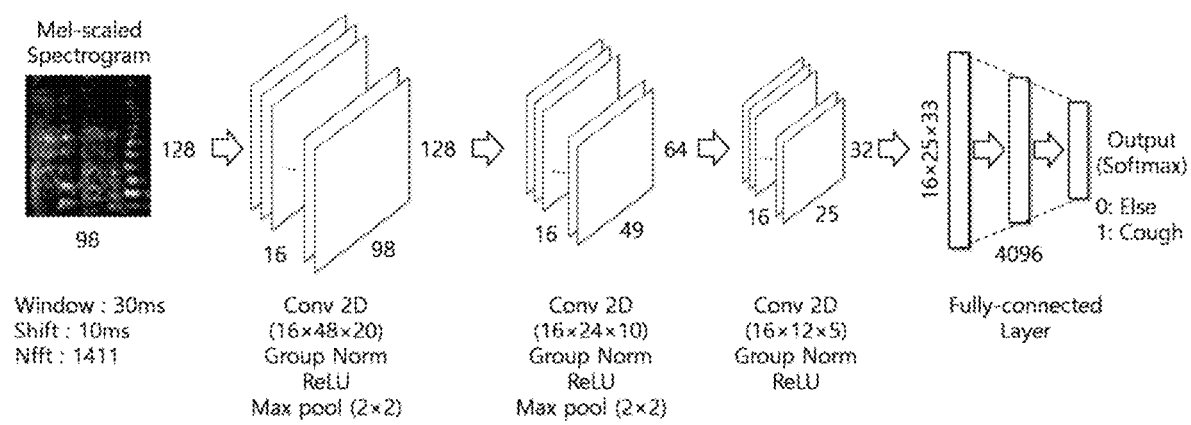
FIG. 1 illustrates an example of a deep learning model according to an example embodiment.
Figure 2:
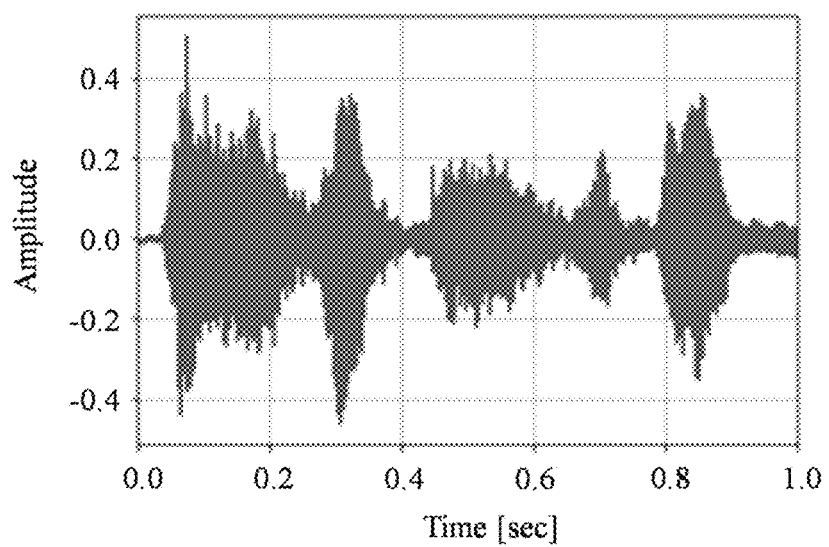
FIGS. 2 to 7 illustrate examples of acoustic features used for learning of a cough recognition model according to an example embodiment.
Figure 3:
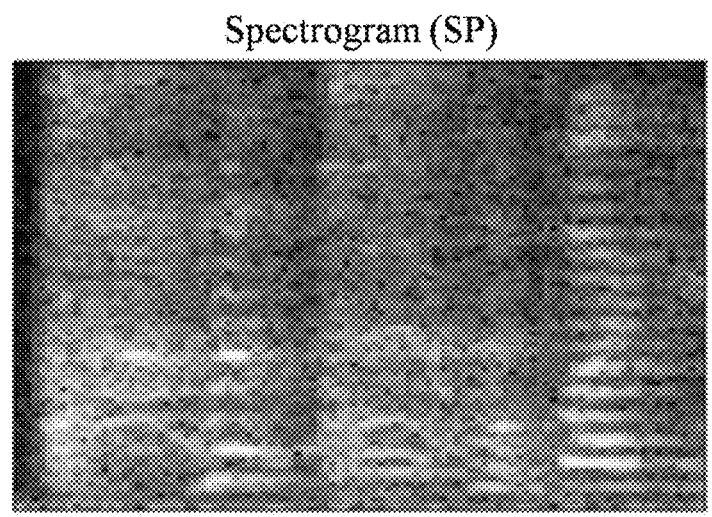
Figure 4:
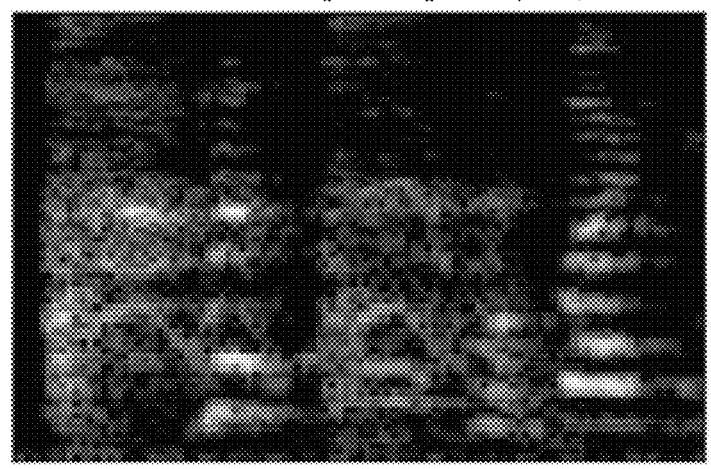
Figure 5:
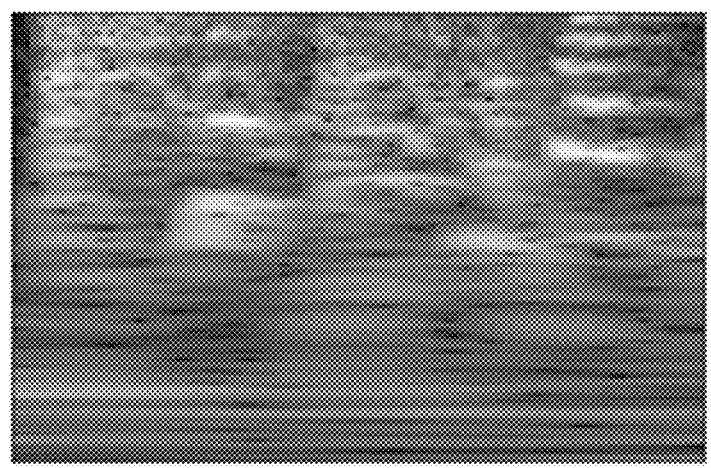
Figure 6:
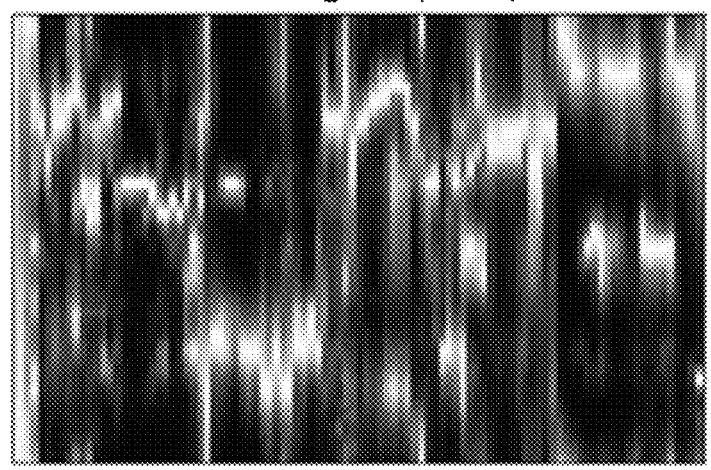

Various modifications may be made to the disclosure and specific example embodiments are illustrated in the drawings and described in detail in the detailed description. However, it should be understood that it is not construed as limited to a specific implementation and should be understood to include all changes, equivalents, and replacements within the idea and the technical scope of the disclosure. Like reference numerals refer to like elements in describing each drawing.

Although terms of "first," "second," "A," and "B," and the like are used to explain various components, the components are not limited to such terms. These terms are used only to distinguish one component from another component. For example, a first component may be referred to as a second component, or similarly, the second component may be referred to as the first component within the scope of the present disclosure. Term "and/or" includes any one and any combination of any two or more of the associated listed items.

When it is mentioned that one component is "connected" or "accessed" to another component, it may be understood that the one component is directly connected or accessed to another component or that still other component is interposed between the two components. In addition, it should be noted that if it is described in the specification that one component is "directly connected" or "directly accessed" to another component, still other component may not be present therebetween.

The terminology used herein is for the purpose of describing particular example embodiments only and is not to be limiting of the example embodiments. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

Hereinafter, example embodiments will be described with reference to the accompanying drawings.

A cough recognition device according to an example embodiment may use a deep learning model trained by receiving learning data that includes data augmented cough sound with background noise. Here, the deep learning model may be a binary classification model configured to receive acoustic features extracted from the audio signals and to classify the audio signals into the cough sound and other sound. For example, the trained deep learning model may receive audio signals input through a microphone of the cough recognition device and to output 1 (cough sound) or 0 (other sound). Here, output 1 (cough sound) may represent a case in which the audio signals include at least the cough sound regardless of whether other sound is included. The output 0 (other sound) may represent a case in which the cough sound is not included in the audio signals. Also, the cough recognition device may include an acoustic camera to make a location of the cough sound trackable. The acoustic camera refers to a camera to which a plurality of microphone arrays is mounted and, when sound is detected, may calculate a location of a sound source and display the location of the sound source on a camera image in a form of a contour line. Therefore, when an output of the cough recognition model is cough sound by applying the cough recognition model, the cough sound may be tracked in real time by displaying a location at which the cough sound occurs on a camera image corresponding to a point in time at which the cough sound is recognized among a plurality of camera images generated by the acoustic camera. Here, the location at which the cough sound occurs may be in a form of displaying the contour line and a cough label at the corresponding location on the camera image.

FIG. 1 illustrates an example of a deep learning model according to an example embodiment. FIG. 1 illustrates a structure of a convolutional neural network (CNN)-based cough recognition model as an example of the deep learning model. The cough recognition model according to the example embodiment refers to a binary classification model. Here, input is a feature of a one-second audio signal and output is 0 (other sound (else)) or 1 (cough sound (cough)). As shown in a first box indicated with dotted lines, a hidden layer may include three convolution layers and two fully-connected layers. Each of the first and second convolution layers may include a two-dimensional convolution (Cony 2D), a group normalization (Group Norm), a rectified linear unit (ReLU), and a maximum pooling (max pool). Also, the third convolution layer may be connected to the first fully-connected layer instead of the maximum pooling. After passing through the second fully-connected layer, an index in which a largest value is acquired through softmax in a binary output layer may be an output result of the deep learning model. For example, if a largest value is acquired first, that is, 0, the input audio signal may be recognized as the other sound (else), and if the largest value is acquired second, that is, 1, the input audio signal may be recognized as the cough sound (cough). A cross entropy is used for a loss function. Learning may be performed by acquiring a differential coefficient of a loss function value for each of model parameters through a back-propagation algorithm and by updating the model parameters with an optimizer. Here, when a learning rate is stagnated for a certain period of time for optimization of the learning rate, the loss function value may be set to decrease.

Figure 7:
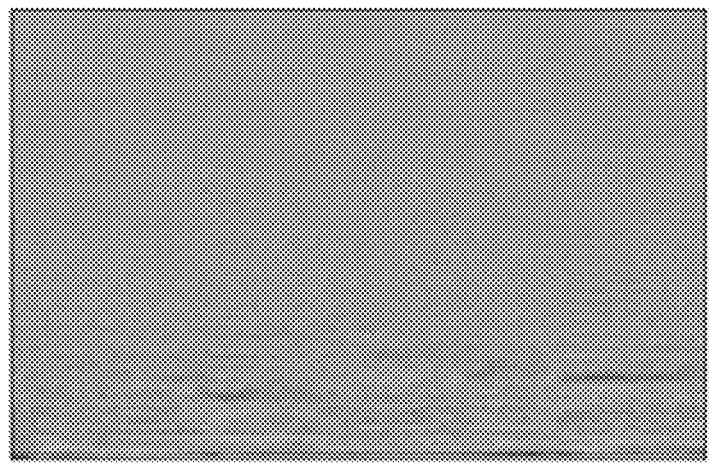

FIGS. 2 to 7 illustrate examples of acoustic features used for learning of a cough recognition model according to an example embodiment. An acoustic feature needs to be extracted from an audio signal to be used as an input value of the cough recognition model. Although there are various acoustic features, a total of five acoustic features, a spectrogram (SP) of FIG. 3, a mel-scaled spectrogram (MS) of FIG. 4, a constant-Q transform (CQT) of FIG. 5, a chromagram (CRM) of FIG. 6, and mel-frequency cepstral coefficients (MFCC) of FIG. 7, are shown as main acoustic features for audio signals that appear in a graph of FIG. 2. All the acoustic features represent a change in frequency characteristic over time and may represent a one-dimensional (1D) audio signal as a 2D feature through acoustic feature extraction. Therefore, a deep learning algorithm, such as a convolution neural network used for the existing image pattern recognition, may be used as the cough recognition model. Data augmentation may use a variety of methods, for example, background noise mixing and distance generalization. Background noise mixing refers to adding background noise to a learning dataset at various ratios and the distance generalization refers to adjusting volume at various scales to be generalized with respect to various distances. A training and validation dataset may be configured by dividing the augmented dataset at a predetermined ratio and a test dataset may use a separately recorded audio signal. The performance of the cough recognition model may be verified with the test accuracy of the test dataset.

Figure 8:
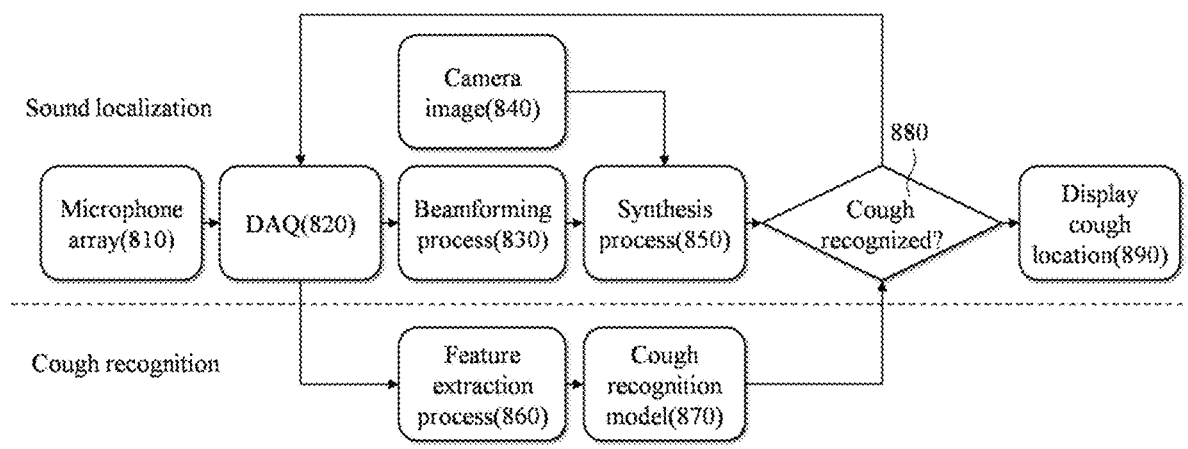
FIG. 8 illustrates an example of a signal processing process of a cough recognition device according to an example embodiment.

FIG. 8 illustrates an example of a signal processing process of a cough recognition device according to an example embodiment. A signal processing system of the cough recognition device may be divided into two main parts. One is a sound localization part and the other is a cough recognition part. Initially describing the sound localization part, when sound is input through a microphone array 810, audio signals may be collected through data acquisition (DAQ) 820. The audio signals may be used to represent a location of a sound source in a form of a contour line through a beamforming process 830. The audio signals represented in the form of the contour line may be synthesized through a camera image 840 and a synthesis process 850. In the cough recognition part, audio signals of the DAQ 820 may be stored in a data stack until the audio signals are accumulated as audio signals in a preset time section (e.g., a one-second time section) and then converted to acoustic features through a feature extraction process 860 and input to a deep learning-based cough recognition model 870. Here, when cough is recognized through an output result of the cough recognition model 870 in a cough recognition process 880, the cough recognition device may display a cough location (890) by displaying a cough label on the camera image 840 in which the audio signals represented in the form of the contour line are synthesized through the synthesis process 850. More precisely, the audio signals represented in the form of the contour line and the camera image 840 in which the cough label is indicated at the location of the sound source may be displayed on the screen in real time.

Figure 9:
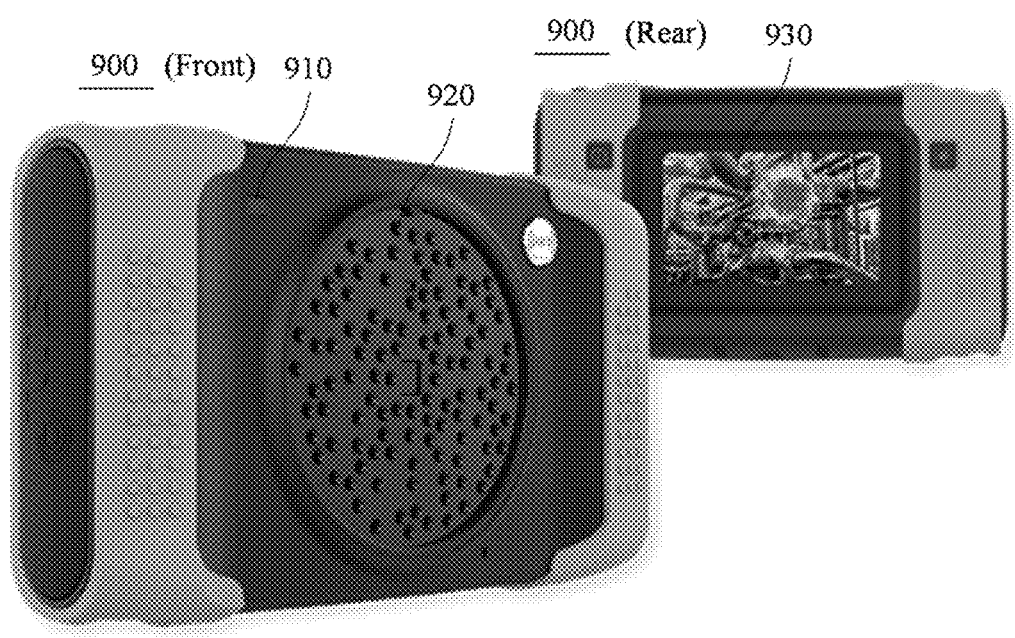
FIG. 9 illustrates an example of a cough recognition device according to an example embodiment.

FIG. 9 illustrates an example of a cough recognition device according to an example embodiment. A camera lens 910 and a plurality of microphones 920 that enables beamforming for localization of a sound source are provided on the front surface of a cough recognition device 900 according to the example embodiment and a liquid crystal screen 930 is mounted on the rear surface of the cough recognition device 900 to display a location on a camera image at which cough has occurred in real time. An output image of the cough recognition device 900 may be transmitted to the outside as well as an embedded liquid crystal screen and a recording function may be provided. Also, the cough recognition device 900 may include a camera module configured to generate a camera image based on an optical signal input through the camera lens 910.

Figure 10:
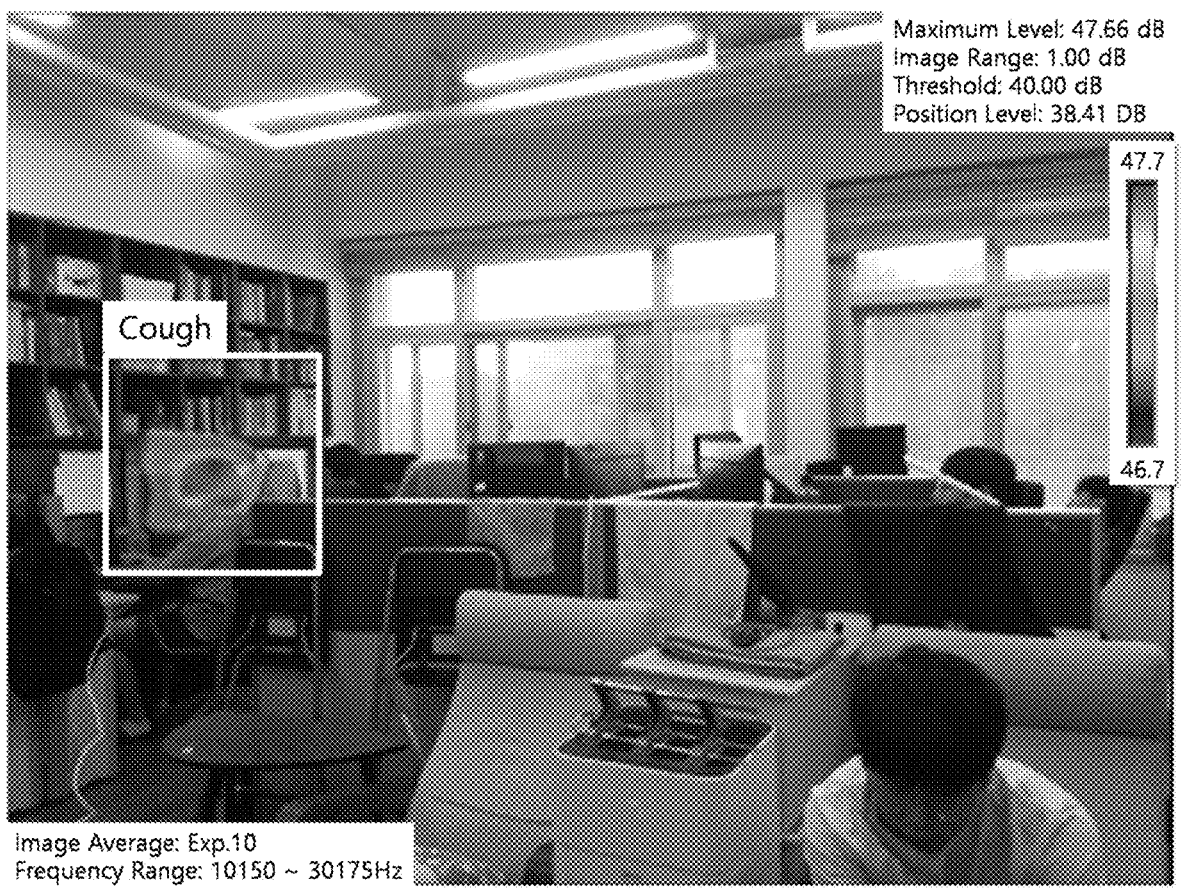
FIGS. 10 and 11 illustrate photos of examples of recognizing, by a cough recognition device, cough and displaying a cough occurrence location according to an example embodiment.
Figure 11:
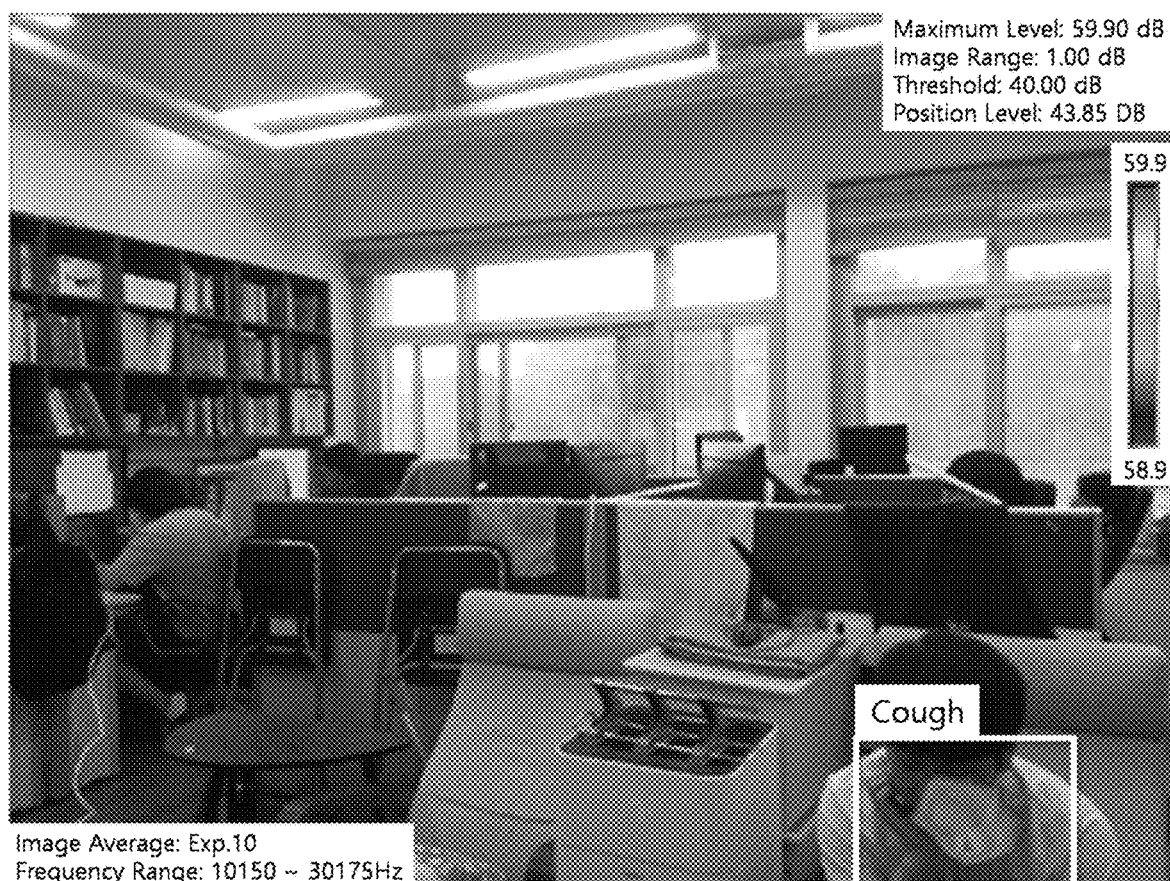

FIGS. 10 and 11 illustrate photos of examples of recognizing, by a cough recognition device, cough and displaying a cough occurrence location according to an example embodiment. Once the cough recognition device is mounted indoors, the cough recognition device may track and observe a location at which cough sound occurs indoors. In particular, when facial recognition technology is applied, it is possible to identify a person and thus, it is possible to observe how many times a specific person coughs for a certain period of time. Using such technology, it is possible to detect the epidemics of infectious disease in advance in a public space, such as a school, a hospital, and an office. In addition, since it is possible to verify a cough history of a patient in the ward according to a time and frequency, it may be used for patient care.

Figure 12:
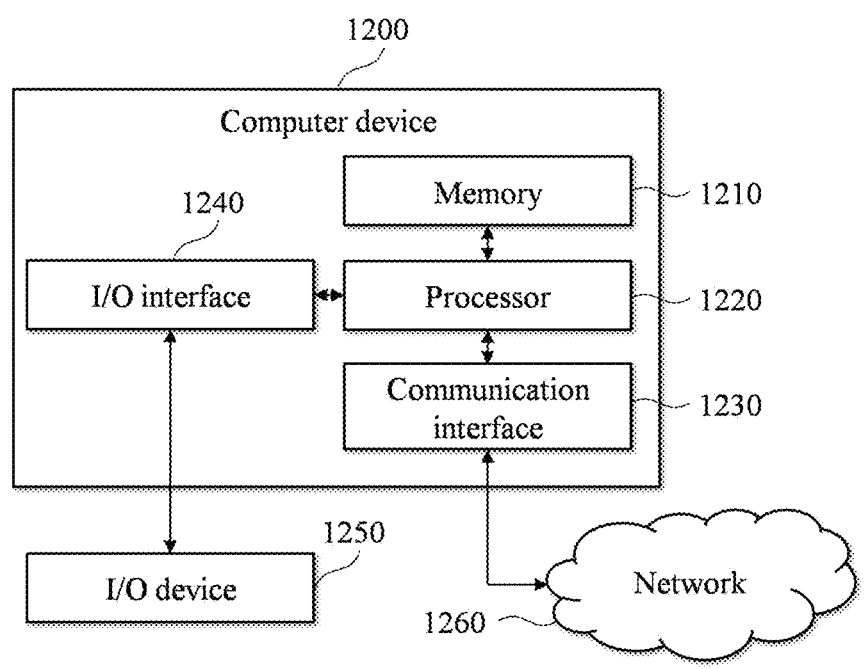
FIG. 12 is a block diagram illustrating an example of an internal configuration of a cough recognition device according to an example embodiment.
Figure 13:
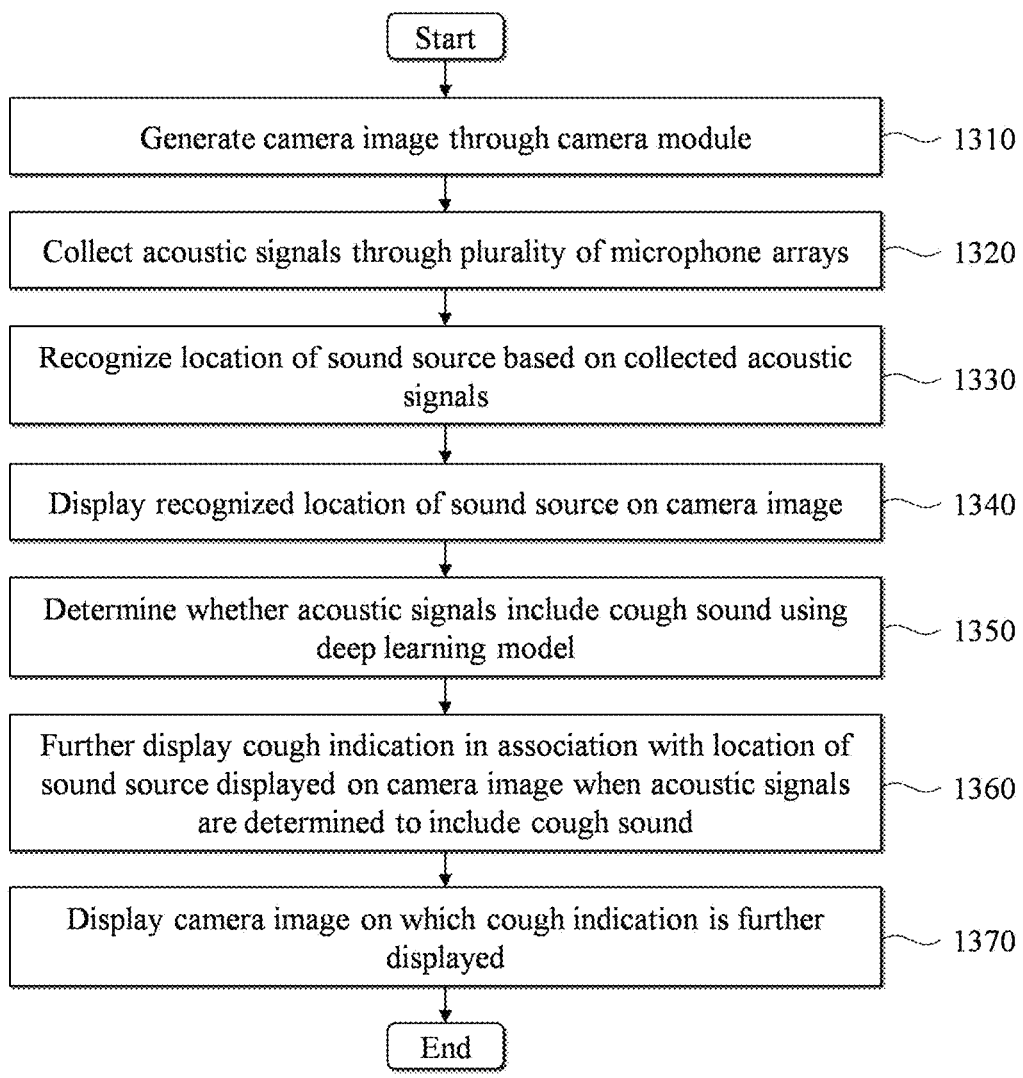
FIG. 13 is a flowchart illustrating an example of a cough recognition method of a cough recognition device according to an example embodiment.

FIG. 12 is a block diagram illustrating an example of an internal configuration of a cough recognition device according to an example embodiment, and FIG. 13 is a flowchart illustrating an example of a cough recognition method of a cough recognition device according to an example embodiment.

The aforementioned cough recognition device (e.g., the cough recognition device 900 of FIG. 9) may be implemented by the computer device of FIG. 12. Referring to FIG. 12, the computer device 1200 may include a memory 1210, a processor 1220, a communication interface 1230, and an input/output (I/O) interface 1240. The memory 1210 may include a permanent mass storage device, such as a random access memory (RAM), a read only memory (ROM), and a disk drive, as a computer-readable record medium. The permanent mass storage device, such as ROM and a disk drive, may be included in the computer device 1200 as a permanent storage device separate from the memory 1210. Also, an OS and at least one program code may be stored in the memory 1210. Such software components may be loaded to the memory 11210 from another computer-readable record medium separate from the memory 1210. The other computer-readable record medium may include a computer-readable record medium, for example, a floppy drive, a disk, a tape, a DVD/CD-ROM drive, a memory card, etc. According to other example embodiments, software components may be loaded to the memory 1210 through the communication interface 1230, instead of the computer-readable record medium. For example, the software components may be loaded to the memory 1210 of the computer device 1200 based on a computer program installed by files received over a network 1260.

The processor 1220 may be configured to process instructions of a computer program by performing basic arithmetic operations, logic operations, and I/O operations. The instructions may be provided from the memory 1210 or the communication interface 1230 to the processor 1220. For example, the processor 1220 may be configured to execute received instructions in response to the program code stored in the storage device, such as the memory 1210.

The communication interface 1230 may provide a function for communication between the communication apparatus 1200 and another apparatus over the network 1260. For example, the processor 1220 of the computer device 1200 may forward a request or an instruction created based on a program code stored in the storage device such as the memory 1210, data, and a file, to other apparatuses over the network 1260 connected through the communication interface 1230. Inversely, a signal, an instruction, data, a file, etc., from another apparatus may be received at the computer device 1200 through the network 1260 and the communication interface 1230. A signal, an instruction, data, etc., received through the communication interface 1230 may be forwarded to the processor 1220 or the memory 1210, and a file, etc., may be stored in a storage medium (e.g., the permanent storage device) further includable in the computer device 1200.

The I/O interface 1240 may be a device used for interfacing with an I/O apparatus 1250. For example, an input device may include a device, such as a camera, a sensor, a microphone, a keyboard, a mouse, etc., and an output device may include a device, such as a display, a speaker, a vibrator, etc. As another example, the I/O interface 1240 may be a device for interfacing with an apparatus in which an input function and an output function are integrated into a single function, such as a touchscreen. At least one of the I/O apparatus 250 may be configured as a single apparatus with the computer device 1200. For example, a touchscreen, a microphone, a speaker, a camera, etc., may be included in the computer device 1200, such as a smartphone. As in the example embodiment of FIG. 9, an example in which the camera lens 910, the camera module, the plurality of microphones 920, and the liquid crystal screen 930 included as the I/O apparatus 1250 are included in the cough recognition device 900 is described.

Also, in other example embodiments, the computer device 1200 may include the number of components greater than or less than the number of components shown in FIG. 12. However, there is no need to clearly illustrate most conventional components. As described above, the computer device 1200 may include at least a portion of the I/O apparatus 1250 or may further include other components, such as a transceiver and a database.

Meanwhile, the cough recognition method according to the example embodiment may be performed by the computer device 1200. Here, the processor 1220 of the computer device 1200 may be implemented to execute a control instruction according to a code of at least one computer program or a code of an OS included in the memory 1210. Here, the processor 1220 may control the computer device 1200 to perform operations 1310 to 1370 included in the method of FIG. 13.

In operation 1310, the computer device 1200 may generate a camera image through a camera module. For example, the camera module may generate the camera image using an optical signal input through the camera lens 910 of FIG. 9. The camera module may continuously generate the camera image and may display the generated camera image on a screen of the computer device 1200 or a screen of another device connected to the computer device 1200.

In operation 1320, the computer device 1200 may collect audio signals through a plurality of microphone arrays. For example, the plurality of microphone arrays, such as the plurality of microphones 920 of FIG. 9, may be formed to receive audio signals in a direction in which the camera lens 910 receives optical signals. Here, the computer device 1200 may collect the audio signals input through the plurality of microphone arrays through DAQ.

In operation 1330, the computer device 1200 may recognize a location of a sound source based on the collected audio signals. For example, the computer device 1200 may recognize the location of the sound source through a beamforming process for the collected audio signals. Here, the recognized location of the sound source may correspond to a specific location on the camera image.

In operation 1340, the computer device 1200 may display the recognized location of the sound source on the camera image. For example, the computer device 1200 may display the recognized location of the sound source on the camera image in a form of a contour line.

In operation 1350, the computer device 1200 may determine whether the audio signals include cough sound using a deep learning model. Here, the deep learning model may include a binary classification model configured to receive and learn learning data including data augmented cough sound with background noise and to output whether the input audio signals include the cough sound. In this case, the computer device 1200 may store the collected audio signals in a data stack to be accumulated in a preset time section, and may extract acoustic features from the audio signals accumulated in the preset time section. Also, the computer device 1200 may input the extracted acoustic features to the deep learning model and determine whether the audio signals include the cough sound based on an output value of the deep learning model. The aforementioned example embodiment relates to an example of outputting a value of 1 when the deep learning model determines that the cough sound is included in the audio signals and outputting a value of 0 when the deep learning model determines that the cough sound is not included in the audio signals. The computer device 1200 may determine whether the audio signals include the cough sound based on such an output value.

In operation 1360, when the audio signals are determined to include the cough sound, the computer device 1200 may further display a cough indication in association with the location of the sound source displayed on the camera image. For example, photos of FIGS. 10 and 11 are examples of displaying label "Cough" as a cough indication.

In operation 1370, the computer device 1200 may display the camera image on which the cough indication is further displayed. Therefore, it is possible to detect whether cough occurs and also to detect and display a cough occurrence location in real time by displaying the cough indication and a location indication in a form of a contour line.

As described above, according to example embodiments, it is possible to detect cough sound from audio signals and also to track a location at which the cough sound occurs by calculating a location of a sound source.

The systems or apparatuses described herein may be implemented using hardware components or a combination of hardware components and software components. For example, the apparatuses and the components described herein may be implemented using one or more general-purpose or special purpose computers, for example, a processor, a controller, an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of the processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combinations thereof, for independently or collectively instructing or configuring the processing device to operate as desired. Software and/or data may be embodied in any type of machine, component, physical equipment, virtual equipment, a computer storage medium or device, to be interpreted by the processing device or to provide an instruction or data to the processing device. The software also may be distributed over network coupled computer systems so that the software is stored and executed in a distributed fashion. The software and data may be stored by one or more computer readable storage media.

The methods according to the above-described example embodiments may be configured in a form of program instructions performed through various computer devices and recorded in computer-readable media. The media may include, in combination with program instructions, data files, data structures, and the like. Here, the media may continuously store computer-executable programs or may transitorily store the same for execution or download. Also, the media may be various types of recording devices or storage devices in a form in which one or a plurality of hardware components are combined. Without being limited to media directly connected to a computer system, the media may be distributed over the network. Examples of the media include magnetic media such as hard disks, floppy disks, and magnetic tapes; optical media such as CD-ROM and DVDs; magneto-optical media such as floptical disks; and hardware devices that are configured to store program instructions, such as read-only memory (ROM), random access memory (RAM), flash memory, and the like. Examples of other media may include record media and storage media managed by an app store that distributes applications or a site that supplies and distributes other various types of software, a server, and the like. Examples of the program instruction may include a machine code as produced by a compiler and include a high-language code executable by a computer using an interpreter and the like.

Although the example embodiments are described with reference to some specific example embodiments and accompanying drawings, it will be apparent to one of ordinary skill in the art that various alterations and modifications in form and details may be made in these example embodiments without departing from the spirit and scope of the claims and their equivalents. For example, suitable results may be achieved if the described techniques are performed in different order, and/or if components in a described system, architecture, device, or circuit are combined in a different manner, and/or replaced or supplemented by other components or their equivalents.

Therefore, other implementations, other example embodiments, and equivalents of the claims are to be construed as being included in the claims.

What is claimed is:

1. A cough recognition device comprising:
   a plurality of microphone arrays configured to receive audio signals;
   a camera module configured to generate a camera image; and
   at least one processor,
   wherein the at least one processor is configured to,
   collect the audio signals through the plurality of microphone arrays and display a location of a sound source on the camera image,
   determine whether the audio signals include cough sound using a deep learning model, and
   when the audio signals include the cough sound, further display a cough indication in association with the location of the sound source displayed on the camera image,
   wherein the deep learning model includes a binary classification model configured to receive and learn learning data including data augmented cough sound with background noise and to output whether the input audio signals include the cough sound,
   wherein the at least one processor is further configured to, when the input audio signals is classified as including the cough sound, displaying a location where the cough sound is generated by displaying the cough label indicating the cough mark along with the location of the sound source on the camera image.

2. The cough recognition device of claim 1, wherein, to display the location of the sound source, the at least one processor is configured to,
   collect the audio signals input through the plurality of microphone arrays through data acquisition (DAQ), and
   display the location of the sound source recognized through a beamforming process for the collected audio signals on the camera image in a form of a contour line.

3. The cough recognition device of claim 1, wherein, to determine whether the audio signals include the cough sound using the deep learning model, the at least one processor is configured to,
   store the collected audio signals in a data stack to be accumulated in a preset time section,
   extract acoustic features from the audio signals accumulated in the preset time section, and
   input the extracted acoustic features to the deep learning model and determine whether the audio signals include the cough sound based on an output value of the deep learning model.

4. A cough recognition method comprising:
   generating a camera image through a camera module;
   collecting audio signals through a plurality of microphone arrays and displaying a location of a sound source on the camera image;
   determining whether the audio signals include cough sound using a deep learning model; and
   when the audio signals are determined to include the cough sound, further displaying a cough indication in association with the location of the sound source displayed on the camera image,
   wherein the deep learning model includes a binary classification model configured to receive and learn learning data including data augmented cough sound with background noise and to output whether the input audio signals include the cough sound,
   wherein, when the input audio signals is classified as including the cough sound, a location where the cough sound is generated is displayed by displaying the cough label indicating the cough mark along with the location of the sound source on the camera image.

5. The cough recognition method of claim 4, wherein the displaying of the location of the sound source comprises:
   collecting the audio signals input through the plurality of microphone arrays through data acquisition (DAQ), and
   displaying the location of the sound source recognized through a beamforming process for the collected audio signals on the camera image in a form of a contour line.

6. The cough recognition method of claim 4, wherein the determining whether the audio signals include the cough sound using the deep learning model comprises:
   storing the collected audio signals in a data stack to be accumulated in a preset time section;
   extracting acoustic features from the audio signals accumulated in the preset time section; and
   inputting the extracted acoustic features to the deep learning model and determining whether the audio signals include the cough sound based on an output value of the deep learning model.

* * * * *